US009095104B2

(12) United States Patent
Miebach et al.

(10) Patent No.: US 9,095,104 B2
(45) Date of Patent: Aug. 4, 2015

(54) **HYBRID CULTIVARS OF *POA BULBOSA***

(75) Inventors: Chad F. Miebach, Aumsville, OR (US); Steven J. Witten, Eugene, OR (US)

(73) Assignee: Radix Research, Inc., Junction City, OR (US)

( * ) Notice: Subject to any disclaimer, the term of this patent is extended or adjusted under 35 U.S.C. 154(b) by 402 days.

(21) Appl. No.: 13/190,437

(22) Filed: Jul. 25, 2011

(65) Prior Publication Data

US 2012/0023604 A1 Jan. 26, 2012

Related U.S. Application Data

(60) Provisional application No. 61/367,077, filed on Jul. 23, 2010, provisional application No. 61/409,321, filed on Nov. 2, 2010.

(51) Int. Cl.
| | | |
|---|---|---|
| *A01H 5/06* | (2006.01) | |
| *A01H 5/10* | (2006.01) | |
| *A01H 5/12* | (2006.01) | |

(52) U.S. Cl.
CPC .. *A01H 5/06* (2013.01); *A01H 5/10* (2013.01); *A01H 5/12* (2013.01)

(58) Field of Classification Search
None
See application file for complete search history.

(56) References Cited

U.S. PATENT DOCUMENTS 5,912,412 A 6/1999 White
2004/0010816 A1* 1/2004 Lee et al. ............ 800/278

OTHER PUBLICATIONS

Westover, H. L. et al., The Bulletin of the United States Golf Association Green Section vol. 7, No. 4; pp. 78-82 published Apr. 1927.*
Ofir, M. et al. Annals of Botany 2014; vol. 113, No. 7 pp. 1249-1256 (presented as pp. 1-8).*
Bulbous Bluegrass, *Poa bulbosa* L., US Department of Agriculture, Natural Resources Conservation Service, Plant Guide, edited Aug. 29, 2007, 4 pages.
Gucker, Corey L., 2007, *Poa Bulbosa*. In: Fire Effects Information System, U.S. Department of Agriculture, Forest Service, Rocky Mountain Research Station, Fire Sciences Laboratory, available at http://www.fs.fed.us/database/feis.
International Search Report and Written Opinion issued in PCT/US2011/045257, mailed Dec. 14, 2011, 7 pages.
Ofir, Micha et al., "Opposite Effects of Daylength and Temperature on Flowering and Summer Dormancy of *Poa bulbosa*", Annals of Botany 97: 659-666, 2006.
Ofir, Micha et al., "Regulation of Summer Dormancy by Water Deficit and ABA in *Poa bulbosa* Ecotypes" Annals of Botany 99:293-299, 2007.
Volaire, Florence et al., "Summer Dormancy in Perennial Temperate Grasses", Annals of Botany 98:927-933, 2006.
Westover, H.L. et al., "*Poa Bulbosa*", The Bulletin of the United States Golf Association Green Section, vol. 7, No. 4, Apr. 1927, pp. 78-82.

* cited by examiner

*Primary Examiner* — Russel Kallis
(74) *Attorney, Agent, or Firm* — Sunstein Kann Murphy & Timbers LLP

(57) ABSTRACT

New hybrid cultivars of *Poa bulbosa* are persistent in a turf setting, and possess multiple characteristics desired in a turfgrass.

17 Claims, No Drawings

HYBRID CULTIVARS OF *POA BULBOSA*

CROSS-REFERENCE TO RELATED APPLICATION

This application claims the benefit of Provisional Application No. 61/367,077, filed Jul. 23, 2010 and Provisional Application No. 61/409,321, filed Nov. 2, 2010, both of which are herein incorporated by reference in their entireties.

BACKGROUND OF THE INVENTION

Bulbous bluegrass (*Poa bulbosa*) is an obscure species of *Poa*, described as a short-lived cool-season grass, and the only grass known to have true bulbs. See, for example, the USDA Plant Guide: Bulbous Bluegrass, available on the UDSA website: plants.usda.gov/plantguide/pdf/pg_pobu.pdf. Introduced into the United States from Europe prior to 1900, *Poa bulbosa* is a bluegrass having a bunching growth habit that is easy to identify from other bluegrasses because of its leafy flowerheads combined with bulbous florets (bulblets). While *Poa bulbosa* produces true florets as well as bulblets, seeds are rare, with regeneration of the plants almost exclusively through asexual means. (Gucker et al., 2007, *Poa bulbosa*. In: Fire Effects Information System [Online], USDA Forest Service, Rocky Mountain Research Station, Fire Sciences Laboratory, available at: fs.fed.us/database/feis/. Each of the clonal bulblets has the potential to form a new plant, identical in nature to the parent plant.

Attempts to cultivate selections of wild ecotypes of *Poa bulbosa* into a commercial turf grass have not been successful. The species was previously found unsuitable due to high variability, low germination, lack of persistence, and competition with companion grasses. *Poa bulbosa* is generally considered a weed to be eradicated.

Currently, there is no cool-season grass species, hybrid, or cultivar having sufficient qualities to be useful as a turf grass, for example as a cool-season component of a sports field. In particular, there is no cool-season grass having utility as a cool-season component for traditional turfgrass overseeding applications on sports fields, fairways, parks, home lawns, and golf course greens that are comprised predominantly of a permanent, warm-season species. There is a need for uniform, reliable varieties of grasses suitable as persistent turfgrass, and particularly useful as a permanent cool-season component in turfgrass overseeding application and having acceptable characteristics for turf, including compatibility with a warm season grass.

SUMMARY OF THE INVENTION

New hybrid varieties of *Poa bulbosa* have now been produced and cultivated that can establish and persist in a turf stand. The new hybrid cultivars provide a population having desirable characteristics, particularly for turf grass applications. In an embodiment, the *Poa bulbosa* cultivars are uniform, and possess a plurality of advantageous characteristics such as resistance to disease, tolerance of multiple soil types, shade, mowing heights, and drought, a healthy vibrant verdure, low and dense growth habit, medium to fine texture, a restricted reproductive habit with good bulblet production, comprehensive seasonal dormancy, rapid emergence and green-up, and relatively uniform transition periods into and out of dormancy. A plurality of these useful characteristics provides a hardy, healthy, and desirable *Poa bulbosa* turf grass.

The new hybrid cultivars of *Poa bulbosa* demonstrate some familiar characteristics that are common to traditional turf grasses, such as texture, vibrancy, and color common to a warm season turf grass such as a commercial Bermuda grass. The new cultivars are capable of developing and persisting in a turf stand, in contrast to wild ecotypes of *Poa bulbosa*, and demonstrate, for example, more aggressive growth, establishment, and/or persistence.

The hybrid *Poa bulbosa* cultivars are persistent in a turf setting, and most preferably are perennial. In an embodiment, a transition period, including one or both of transition into dormancy and transition out of warm-season dormancy, complements the growth habit of a warm season grass, such as Bermuda grass. In an embodiment, the new cultivars provide a suitable cool-season component of a turf stand, such as a sports field, golf course playing field, park, home lawn, and the like. In an alternative embodiment, the *Poa bulbosa* cultivars include one or more preferred characteristic and are useful as parents for breeding the preferred characteristic(s) into hybrid progeny.

Representative bulblets of the hybrid cultivars of *Poa bulbosa* were deposited under the terms of the Budapest Treaty with the American Type Culture Collection in Manassas, Va. USA and were given the ATCC Accession Numbers shown below:

| Hybrid | ATCC# |
| --- | --- |
| 6PB20 | PTA-11181 |
| 6PB22 | PTA-11228 |
| 6PB25 | PTA-11182 |
| 6PB26 | PTA-11183 |
| 6PB27 | PTA-11187 |
| 6PB28 | PTA-11188 |
| 6PB29 | PTA-11189 |
| 7PB2 | PTA-11184 |
| 7PB42 | PTA-11229 |
| 7PB48 | PTA-11185 |
| 7PB51 | PTA-11230 |
| 7PB55 | PTA-11186 |

Disclosed herein are hybrid cultivars of *Poa bulbosa* useful as a cool-season component of a turf. The hybrid cultivars possess all the essential characteristics and all the morphological and physiological characteristics of one or more of the new hybrid cultivars designated above, and preferably possess desirable turf quality characteristics contributed by one or more of the hybrid cultivars designated above. The invention further includes progeny (e.g., clonal, apomatic, or hybrid) derived from one or more of the hybrid cultivars, as well as portions such as vegetative plant tissue, bulbs, bulblets, seed, florets, aerial clones, cells, and the like, and plants derived from such plant parts.

The hybrid cultivar(s) can form a turf stand, such as a sports field, golf green or fairway, playing field, park, lawn, and the like, comprising a hybrid cultivar of *Poa bulbosa* that is preferably persistent and/or perennial. In an embodiment, the *Poa bulbosa* cultivar(s) comprises a cool-season component of a multi-component turf stand, for example, that also comprises a warm-season grass. Methods of producing a turf stand include the steps of planting and growing a hybrid *Poa bulbosa* cultivar to form a turf stand. The *Poa bulbosa* turf stand can be grown, for example, from vegetative tissue, bulbs, bulblets, florets, aerial clones, or from seed derived from a hybrid *Poa bulbosa* cultivar.

One or more hybrid *Poa bulbosa* cultivar can be used as a parental line in a method for producing a hybrid plant having one or more desired characteristic of the parent.

The invention further includes lawns, turf, sporting fields, and the like, comprising a *Poa bulbosa* cultivar of the invention, as well as kits and systems for producing a turf comprising the *Poa bulbosa* cultivar(s), or a portion thereof, such as bulblets. The kit or system may further comprise a companion seed, for example, of a warm season grass, growth nutrients, and/or instructions for planting and growth. The turf can be, for example, a sports turf, golf fairway, golf green, park, lawn, and the like.

DETAILED DESCRIPTION

Definitions

"Cultivar", as used herein, defines a plant line selected for desirable characteristics that has been cultivated by one or more of selection, breeding, and hybridization to provide a cultivated line that is true to type.

"Bulb", as used herein, refers to that underground portion of a *Poa bulbosa* plant from which shoots emerge to form a growing plant. Growth points on each underground bulb are capable of producing additional underground bulbs that result in spreading of the above ground vegetation. In this way, the size and spread of the above ground crown is influenced by the size and function of the underground bulb(s).

"Bulblet", as used herein, refers to aerial clonal bulblets that form the main reproductive tissue of *Poa bulbosa*. Panicle-bearing culms are induced during the determinant reproductive period of *Poa bulbosa*, generally during the end of the plant's growing season. The culms may be induced by increased temperatures and decreased moisture. Bulblets form on the panicles, each of the bulblets having the potential to produce a complete *Poa bulbosa* plant identical to the parent plant. Like seed, bulblets can be harvested, dried, and planted to produce growing *Poa bulbosa* plants.

"Seed", as used herein, refers to sexually produced seed derived from the combination of male and female parent reproductive tissues, and is distinguished from the clonal bulblets defined above. *Poa bulbosa* reproduces almost exclusively vegetatively in a "proliferative" reproductive habit. While some rare ecotypes can develop "non-proliferative" seed-producing panicles, and seed production may sometimes be induced under certain climatic conditions, viable *Poa bulbosa* seed is generally not produced in the wild.

"Persistence" as used herein describes at least 50 percent reestablishment in a turf stand after dormancy under standard growing conditions.

"Reestablishment" as used herein, is a measure of cultivar reemergence and growth after a period of dormancy. Reestablishment may be evaluated as a percent of plot coverage of growing shoots at a particular time period, for example, calculated from date of planting, date of shoot emergence, and the like. For evaluation of persistence, re-establishment is generally analyzed during midseason, for example, from mid-December to mid-February. In preferred embodiments, the cultivars of the invention exhibit at least 50-100% reestablishment, for example, at least 50%, at least 60%, at least 70%, at least 80%, at least 90%, at least 95%, or at least 98%.

"Perennial", as used herein, defines a growth habit where the *Poa bulbosa* cultivar demonstrates persistence more than two years in a turf setting under standard growing conditions.

"Cool Season Grass" as used herein, refers to grasses that grow well during cold winters with temperatures that fall below freezing and are not green during the heat of summer. Examples of cool season grasses include *Poa bulbosa*, bluegrass, fescue, and ryegrass.

"Warm season Grass" as used herein, refers to grasses that grow well during summer heat and are not green during the cold of winter. Leaves brown in late fall and green up again when warm weather returns. Examples of warm season grasses include Bermuda grass, Centipede grass, St. Augustine grass, Kikuyu grass, and Zoysia grass.

"Comprehensive Dormancy" as used herein, refers to complete, total dormancy, with no remaining living ground cover.

New Hybrid Cultivars *Poa bulbosa*

*Poa bulbosa* is a term used to describe a widely variable and highly polymorphic species of grass, and significantly, the only cool-season grass species known to produce and reproduce primarily by true bulbs and clonal bulblets. New, useful, persistent and/or perennial hybrid cultivars have now been bred and selected with desirable characteristics that come true from bulblets or seed. The new cultivars have specific features for use as a persistent, preferably perennial, cool-season component of sports fields, fairways, parks, home lawns, and golf course greens, without the troublesome characteristics of the wild-type *Poa bulbosa* weed.

The novel hybrid cultivars of the present invention were derived by selection and hybridization of collected *Poa bulbosa* plants that appeared to contain one or more desirable trait for turf not apparent in the general populations of *Poa bulbosa* ecotypes. Plants were individually collected from multiple locations and from public depositories as identified below. Upon collection, bulblets or live plants were accessioned with a given collection number, and bulblets from each were germinated in greenhouse trays, in a standard potting mix of peat, sand, and Perlite and grown under standard greenhouse culture. From each line, bulblets were seeded and plants produced for evaluation and selection.

Lines exhibiting one or more desirable turf characteristic such as superior vigor, dense and leafy vegetative tillers, healthy green verdure, restricted reproductive habit, comprehensive dormancy, relatively good post-dormancy regeneration (persistence), good performance under low to moderate fertility conditions, tolerance of low mowing heights (for example, to ½ inch), and the like, were selected and propagated from clonal bulblets or apomictic seed through successive generations, resulting in a production of cultivars having no obvious variants, the lines remaining true to type.

Breeding

*Poa bulbosa* is predominantly and almost exclusively a proliferated species by nature, reproducing asexually by clonal bulblets. Some plants have the capability, however, in varying degrees and depending on the plant's genetics, to change reproduction mode from asexual proliferation to sexual non-proliferation of seed panicles. Cooler temperatures, available moisture, and reduced light can induce a gradual transition from producing proliferated panicles to producing non-proliferated panicles, and eventually producing sexual panicles having flowers capable of giving and receiving pollen, and susceptible to common hybridization techniques. Using such methods to induce sexual panicle production, hybrid *Poa bulbosa* cultivars were successfully produced, bred, and developed through common hybridization procedures. Hybridizations were generally performed in an isolated, greenhouse setting.

Selection Process and Criteria

Initial collections of *Poa bulbosa* and subsequently produced hybrids were selected for a number of characteristics desired in turfgrass. These characteristics include post-dormancy regeneration of crowns, healthy green color, increased density, wear tolerance, fine to medium turf texture, uniformity, tolerance of extreme temperatures, reduced bulblet dormancy period, increased bulblet production, complimentary growth period to that of a companion warm-season grass, mowing tolerance, and the like.

Seed from each hybridized line was germinated in greenhouse trays, in a standard potting mix of peat, sand and Perlite and grown under standard greenhouse culture. Germinated plants were planted in-field to evaluate successful hybridization and to select potential new cultivars having improved turf characteristics. Continued selection and breeding was performed to obtain uniformity in characteristics such as vigor and persistence, as well as desirable turf characteristics, including rapid establishment, stand persistence and regeneration, good color and density, line to medium turf texture, texture comparable to a companion grass during transition phases, minimal disease susceptibility, acceptable bulblet yield, good performance under conditions of moderate to low fertility, comprehensive warm-season dormancy, tolerance to mowing and sports traffic, and the like. Superior individual lines of *Poa bulbosa* were created and identified through this successful hybridization and selection process.

Post-Dormancy Regeneration

It is preferred in a turf setting that grass persist after dormancy, and may be perennial in nature. In many sports or other turf settings, a persistent and preferably perennial variety is desired. Wild-type *Poa bulbosa* lines have tow levels of post-dormancy regeneration and persistence in a continuous turf setting. This may be due to dormant state disease susceptibilities, insufficient carbohydrate storage, poor propagation, and/or subsequent poor persistence of underground bulbs. The hybrid cultivars of *Poa bulbosa* described herein have significantly improved persistence and regeneration from underground bulbs, while retaining comprehensive warm-season dormancy in a continuous turf setting, and present a variety of desirable turf characteristics.

Color

A healthy, vibrant, green color in turfgrass is the aesthetic preference for most applications in sports and other turf settings. Color is also related to chlorophyll content and plant activity rates. The new hybrid *Poa bulbosa* cultivars have a uniform verdure ranging from gray-green to blue-green to bright or dark-green and with improved vibrancy. Color may be selected to match or complement a warm season grass, for example, vibrant green Bermudagrass and Zoysia grass and lighter green St. Augustine.

Density, Texture, and Wear Tolerance

Density is determined by leaf texture, type, and number per unit area. The new *Poa bulbosa* cultivars were selected for medium to fine leaf texture with upright and densely packed leaves sufficient to support mechanical wear of a sports turf as well as functional support, for example, of a golf ball. This density and texture provides a hardy turf tolerant to traffic and wear.

Dormancy

The *Poa bulbosa* cultivars described herein were selected and bred for uniform dormancy characteristics, including comprehensive, above-ground, warm-season dormancy. Utility of the cultivars as a cool-season grass component in a turf comprising a warm-season grass is demonstrated in the hybrid *Poa bulbosa* cultivars, which exhibit dormancy that complements the emergence and growth of the warm-season grass component, permitting adequate emergence and growth of the warm season grass and providing a visually appealing turf over both seasons. Unlike other cool-season grasses such as ryegrass, the *Poa bulbosa* cultivars complement and do not compete with or damage a companion warm-season grass such as Bermuda grass. The new hybrid cultivars of *Poa bulbosa* demonstrate relatively uniform transient phases into and out from warm season dormancy that are preferably complementary to the growth period of a warm season grass, for example one or more variety of Bermuda grass. The comprehensive dormancy of the new cultivars permits good emergence and growth of a companion warm season grass.

Plant Habit and Yearly Cycle

*Poa bulbosa* bulblets or seeds are generally planted in the fall and germinate relatively quickly. Some genetic lines germinate more quickly than others, but most express an emergence of photosynthesizing scutellum shoots (initial top growth), and radicles (initial rooting) within 3 to 6 days in constant conditions of about 60 to 65° F., with low-level lighting and about 8 to 9 hours of day-length. After about 9 to 12 days, plants generally show second leaf emergence.

The new hybrid *Poa bulbosa* cultivars establish best when planted in the fall season. The species grows vegetatively during the winter at varying rates, depending upon genetics and environmental conditions. Some lines establish very quickly and vigorously, while others are slower to establish. Different plant profiles are noted: some plants have a high crown (or growing point) suggesting more suitability to a golf fairway application, others have a very low or more prostrate crown suggesting the possibility of use in the golf greens application.

In western Oregon, a shift into the reproductive stage generally occurs sometime in March. There is significant variability in spring reproductive timing and bulblet maturity between lines. Generally, proliferated, vegetative bulblets reach heading about April $1^{st}$ to May $10^{th}$; and are generally ready for harvest about May $5^{th}$ to June $15^{th}$, depending on genetics and climatic factors. Total plant height ranges from 15-70 cm at maturity in an un-mowed state and including panicles.

Bulblet Production

A desirable turfgrass for sports or commercial applications produces sufficient bulblets (or seed) to support commercial production. It is also preferred that the bulblets can be harvested by standard and/or other uncomplicated methods. *Poa bulbosa* bulblets can be harvested with traditional methods, for example, by direct-combine or swather-combine procedures. After harvest, bulblets are generally processed before cleaning to polish and remove residue from the vegetative bulblet, for example, through a de-bearding machine. Bulblets are generally stored at cool temperatures, preferably about 50° F. and about 30% moisture.

Bulblets of different genetic lines can vary in size, shape and weight, and in bulblet yield per plant. The shape of the bulblets is generally oval to ovate. A smooth oval shape may be preferred for efficient processing with standard machinery. The size of the bulblets generally ranges from about 100,000 to 350,000 bulblets per pound. In general, cultivars exhibiting finer leaf textures tend to produce smaller bulblets.

When the hybrid plants are grown in spaced plantings, the above-ground vegetative growth of one bulblet generally spreads during a first growth year to about 40-50 mm in diameter, and to about 70 to over 100 mm during a second season.

*Poa bulbosa* plants can be produced, for example, by planting and growing seed or bulblets of the hybrid *Poa bulbosa* cultivars, or from vegetative growth obtained from one or more plant part or portion, including bulbs, roots, stems, seed, bulblets, flowers, pollen, ovule, leaf, embryo, meristem, and the like, or from a culture of tissue or cells obtained from the hybrid cultivars.

Hybrid *Poa bulbosa* plants can also be produced by crossing one *Poa bulbosa* cultivar with another *Poa bulbosa* plant. Transgenic *Poa bulbosa* plants can be produced by inserting a transgene into the genome of a *Poa bulbosa* hybrid cultivar, for example a transgene that confers resistance to a disease such or pest, tolerance to a climatic condition or soil element, or that provides the cultivar with a selected trait.

Desired Characteristics

New *Poa bulbosa* cultivars described in this application are stable to type, and present a plurality of characteristics suitable for a variety of commercial uses, for example, for use as a turf grass component of sports fields, fairways, parks, golf park greens, and lawns. These characteristics are described further in the text and Examples below, and include a restrictive, predominantly asexual reproductive habit occurring exclusively in the spring, and vegetative growth beginning in late fall and continuing through winter and spring in milder climates, until high temperatures and long day length induce a comprehensive seasonal dormancy. Desirable turf characteristics also include good vibrant color, acceptable density, tolerance to mowing, rapid cool season emergence and establishment, comprehensive warm season dormancy, persistence, good bulblet yield, and vigor. The new cultivars include those that are useful in over-seeding applications, for example, as a cool season component of a turf that includes a warm season grass.

The new hybrid cultivars are persistent and/or perennial in a turf setting, and have desirable characteristics not commonly found in wild type *Poa bulbosa*. In some embodiments, the cultivar demonstrates persistence of at least 50%, at least 60%, at least 70%, at least 80% or at least 90% cool season reemergence after dormancy in a turf setting. In some embodiments, the cultivar has a cool season growth period and a warm season dormancy period that is compatible with the growth period of a warm season grass, for example Bermuda grass. In some embodiments, plants are selected for rapid transition into or out of dormancy. In some embodiments a later transition-out timing, e.g., plants demonstrating later maturity into dormancy after the reproductive stage, are selected to match with the growth period of a selected warm season grass, such as a Bermuda grass variety.

In Western Oregon, the cultivars have a restricted cool season growth period of about 5 to about 7 months, with persistence of at least 50% reestablishment after comprehensive dormancy, and in some embodiments at least 60%, at least 70%, at least 80%, or at least 85% reestablishment.

The new cultivars of *Poa bulbosa* demonstrate uniformity in a plurality of the following characteristics: restricted reproductive habit; fine to medium leaf texture; vibrant verdure that may be green, green-blue, blue-green, or grey-green, tolerance to mowing, germination, emergence, dormancy, establishment, stand persistence, regeneration, density, flowering, and bulblet yield. One or more of these characteristics is improved as compared to a suitable control, for example, to a wild ecotype of *Poa bulbosa*, or to another hybrid cultivar described herein.

*Poa bulbosa* cultivars were evaluated according to desired turf characteristics, including bright color, leaf texture, density, living ground cover, plant vigor/establishment, winter green-up, disease/insect damage, drought tolerance, frost tolerance, traffic tolerance, thatch accumulation, seed heads, mowing quality/steaminess, overall quality, and the like. Turf characteristics were evaluated according to the National Turfgrass Evaluation Program standards, described, for example at the website: ntep.org/reports/ratings.htm. Winter green-up was evaluated according to the standards set forth for spring green-up by the National Turfgrass Evaluation Program.

National Turfgrass Evaluation Program ratings are generally assessed visually and scored with a range of 1-9, with a score of 1 being the least favorable for the characteristic being evaluated and a score of 9 indicating most favorable. For each characteristic, a score of about 5.0 or greater is considered acceptable, and 6 or greater is preferred. The standard is a relative standard, idealized to a particular species, functional environment, and the like, rather than a universal reference standard. For example, the idealized standard for *Poa bulbosa*, a cool season grass, will differ from the idealized standard for a warm season Bermuda grass. The ideal shoot density for a putting green will differ from that of soccer field turf, for example. The "best possible" and "poorest possible" ratings will be that considered for desired qualities of the particular species and functional use. Turf quality is rated for a plurality of individual desirable characteristics, and an overall "turf quality score" represents a mean score, potentially weighted according to the most desirable characteristics, in some embodiments, additional characteristics are scored and/or measured. For example, leaf length, leaf width, growing and reproductive habit, and bulblet or bulb weight can be measured using known methods.

The weight of an individual characteristic as a component of the overall turf quality depends on the importance of the component in the overall perceived quality of the turfgrass. The importance of a particular component will vary with the intended use of the turf, for example, as a golf green, soccer field, and the like. Some components such as color, are weighted more heavily for uses requiring, a higher degree of visual aesthetic appeal. Other components, such as putting green, may place more weight on components related to the roll of a ball on the turf, such as shoot density and leaf orientation. For *Poa bulbosa* as a turfgrass, quality characteristics generally are rated best or poor as summarized in Table 1.

Rating Characteristics

Uniformity

Uniformity is the degree to which a turfgrass is free from variation in desirable characteristics, including, for example, density, leaf texture, growth habit, response to mowing, smoothness, color, functional use, reproductive habit, and others. Non-uniformity (variation) is generally rated negatively, e.g., on the low side of the 1 to 9 visual scale or numerically as a percentage of the plot having the desired selection characteristic. Typically, for good uniformity in a sports turf, less than 10% of the plants will vary from type, preferably less than 5%, most preferably, less than 1%. Because the *Poa bulbosa* cultivars reproduce clonally, each bulblet is an exact copy of its parent, and variation is minimal, if at all.

TABLE 1

Turfgrass scores.

| Turf Quality Characteristic | 9 "best possible" | 1 "poorest possible" |
|---|---|---|
| Overall Turfgrass Quality | Outstanding or ideal | Dead |
| Uniformity | Good uniformity | Poor uniformity |
| Growth period | Mid-October-Mid April | Early May-Mid October |
| Dormancy period | Early May-Mid October | Mid October-Mid April |
| Living ground cover Jan-Feb | High [100%] | Low [0%] |
| Living ground cover Aug-Sept | Low [0%] | High [100%] |
| Stand persistence | 100% reestablishment | 0% reestablishment |
| Transition timing | Fast | Slow |
| Establishment rate | Rapid | Slow |
| Emergence | Quick | Slow |
| Shoot density | Maximum density | Low density |
| Leaf texture | Fine or Medium | Coarse |
| Leaf orientation | Upright | Random |

TABLE 1-continued

Turfgrass scores.

| Turf Quality Characteristic | 9 "best possible" | 1 "poorest possible" |
|---|---|---|
| Color | Vibrant green, blue-green, grey-green | Dull green, blue-green, grey-green |
| Bulb persistence | High [100%] | Low [0%] |
| Bulb size | High | Low |
| Bulblet number | High | Low |
| Steminess | None | Many |
| Response to Mowing | Clean cut, no damage | Rough cut, shredding, visible damage |
| Disease resistance | Complete resistance, no damage | No resistance, 100% damage |
| Traffic tolerance | Complete resistance, no injury | No resistance, 100% injury |
| Bulblet yield | High | Low |

Living Ground Cover

Living ground cover is generally expressed as a percentage of the plot area that contains live grass. It is used as a relative measure of turf damage due to disease, insects, weed encroachment, mowing, or other stress. Living ground cover ratings can be collected over multiple time points to track turf grass response to stress during the growing season.

In general, for rating turf quality, ground cover is determined during midseason (mid-December to mid-February) and can serve as a measure of reemergence after dormancy, a measure of persistence, and/or a measure of timing and quality of the transition-in or transition-out periods, for example to match with a warm season grass.

Reemergence/Persistence

An important criteria for nearly all turf conditions is that the grass be persistent, and preferably perennial in nature. While there are some applications in which an annual variety can be useful, in most applications for sports or other turf settings, a perennial is desired. Poa bulbosa hybrid cultivars provided herein demonstrated significantly improved persistence and reemergence from underground bulbs while retaining comprehensive warm-season dormancy in a permanent and continuous turf setting as compared to wild Poa bulbosa, in some embodiments, the cultivars are demonstrated to be perennial, that is, to persist for more than two years.

Transition Timing

Transition timing is the relative date and speed by which a cultivar reemerges from dormancy (transition-in) or transitions into comprehensive dormancy after the growing period (transition-out). The hybrid cultivars of Poa bulbosa described herein have improved transition timing as compared with wild type controls. Poa bulbosa cultivars are selected for comprehensive, warm-season dormancy, as well as uniform and/or relatively timed transition periods that can be fast or stow, and can be matched to complement a companion warm-season grass.

Activity Rate

Activity rate is a measure of a plant's vigor, and includes establishment rate, seasonal growth, rate of repair from climatic and disease factors, as well as wear and tear from traffic, mowing, and the like. Activity rate is evaluated qualitatively.

Establishment Rate

Establishment rate (i.e., plant vigor) is evaluated by determining or estimating several factors that reflect the relative speed a cultivar develops into a mature sod, such as percent ground cover, plant height, and the like.

Density

Density is evaluated by examining the number of living plants or tillers per unit area, with dead patches excluded. Density can be measured physically as a number of shoots per unit area, for example, shoots per $in^2$ or $cm^2$, or can be visually rated, with a rating of 9 being maximum density. Density ratings are collected at more than one time point to account for seasonal variation.

Leaf Texture

Leaf texture is a measure or estimate of leaf width. Texture can be measured physically or rated on a scale of 1 to 9 with 1 as broad and 9 as fine. Leaf texture assessment should be done when the turfgrass is actively growing and not under stress.

Leaf Orientation

Leaf orientation is the point of direction of shoots. Leaf orientation is measured on a scale of 1 to 9, with a rating of 1 being random, and a rating of 9 being upright. Cutting or mowing direction can influence leaf orientation.

Color

Genetic color and seasonal color/color retention can be evaluated for Poa bulbosa cultivars. Genetic color is inherent to the genotype of the cultivar, and is evaluated when the cultivar is actively growing and not under stress. It is visually rated with a score ranging from 1 for light green to 9 for dark green. Seasonal color/color retention measures the overall plot color and can be used to identify color differences caused by disease, pests, nutrient deficiency, and stress. Seasonal color/color retention is rated on a scale of 1 to 9, with 1 being straw brown and 9 being dark green.

A healthy green grass is the aesthetic preference for most applications in sports and other turf settings. Color is also related to chlorophyll content and plant activity rates. The new hybrid cultivars described herein have verdure ranging from gray-green to blue-green to dark-green, and preferably exhibit a vibrancy or brightness. Color may be selected to match a companion warm season grass, for example Bermuda grass.

Seedheads

Seedheads are generally considered unsightly and reduce the quality of a turf stand. Seedheads are generally rated on a scale from 1 to 9, with a rating of 9 equaling no seedheads. While Poa bulbosa does not generally produce seedheads, its reproductive panicles and florets are considered unsightly in a turf stand. Poa bulbosa plants are rated for "seedheads" according to the appearance of either sexual (rare) or clonal (usual) reproductive panicles.

Response to Mowing

Some turf grasses may exhibit poor quality after mowing. Poor quality may be due to large numbers of stems produced by the plants during the reproductive phase of their growth cycle. Response to mowing also reflects the uniformity and cleanness of cut exhibited by some grasses. The rating scale is 1 to 9 with 1 equal to poorest mowing quality and most steaminess, and 9 equal to cleanest cut, no steminess. In general, turfgrass is rated for mowing from 2½ inches to ½ inch.

Disease/Insect Resistance

Evaluated plants are assigned a rating for disease and/or insect resistance with a rating of 1 indicating no resistance or 100% injury and 9 indicating complete resistance or no injury. Disease and insect resistance is generally evaluated in a field where exposure to disease is likely and comparing overall performance with a suitable control. Ratings are provided in relation to suitable control plants such as wild ecotypes or other cultivars of Poa bulbosa, warm season grasses, and the like.

Traffic Tolerance

Traffic tolerance is the combination of wear and compaction stress that occurs whenever a turf is exposed to foot traffic or vehicular traffic, or sports ball, club, or other stress. Wear injury occurs immediately upon trafficking a turf with injury symptoms often expressed within hours and definitely within days. Compaction stress injury is more chronic, and is expressed over time. Traffic tolerance is a visual estimate of turfgrass tolerance using a 1 to 9 rating scale with 1 indicating no tolerance or 100% injury, and 9 indicating complete tolerance or no injury.

Bulblet Yield

A desirable turfgrass of hybrid *Poa bulbosa* for sports or commercial applications produces sufficient bulblets to support commercial production, for example in an amount of about 2000-3000 pounds of bulblets per acre.

Growth Habit

The *Poa bulbosa* hybrid cultivars include lines having a high crown or growing point, suggesting suitability for a golf fairway application, as well as others that have a low or prostrate crown suggesting possible use in a golf greens application.

Drought Tolerance

Drought tolerance is assessed by evaluating the leaf to show one of wilting, leaf firing, dormancy, or recovery. Drought tolerance ratings of 1 to 9 are visually determined with a score of 1 indicating complete wilting, 100% leaf firing, complete dormancy, or no plant recovery and a score of 9 indicating no wilting, no leaf firing, 100% green, and no dormancy, or 100% recovery.

Frost Tolerance

Frost injury is expressed on a 1 to 9 rating scale with 1 indicating 100% leaf injury and 9 indicating no injury.

Bulblet Deposits

A deposit of clonal bulblets obtained from the new hybrid *Poa bulbosa* cultivars described in this application and recited in the appended claims has been made with the American Type Culture Collection (ATCC), 10801 University Boulevard, Manassas, Va., 20110. The deposits were made on Jul. 7, 2010 (6PB20, 6PB25, 6PB26, 6PB27, 6PB28, 6PB29, 7PB2, 7PB48 and 7PB55) and Jul. 22, 2010 (6PB22, 7PB42 and 7PB51) under the terms of the Budapest Treaty. Access to deposited material will be available, during pendency of a patent application making reference to it, to anyone determined by the Director to be entitled to access under 37 CFR 1.14 and 35 USC 122 (35 USC 114). Subject to paragraph (b) of 37 CFR 1.808, all restrictions imposed by the depositor on the availability to the public of the deposited material will be irrevocably removed upon the granting of the patent. All restrictions upon the deposit will be removed upon granting of a patent. The deposit will be maintained in the depository for a period of 30 years or 5 years after the last request, or for the effective life of the patent, whichever is longer, and will be replaced as necessary during that period.

The ATCC Accession Numbers for each deposited cultivar are shown in Table 2 below:

TABLE 2

*Poa bulbosa* Cultivar Accession Numbers.

| Cultivar | ATCC Accession No: |
| --- | --- |
| 6PB20 | PTA-11181 |
| 6PB22 | PTA-11228 |
| 6PB25 | PTA-11182 |
| 6PB26 | PTA-11183 |
| 6PB27 | PTA-11187 |
| 6PB28 | PTA-11188 |
| 6PB29 | PTA-11189 |
| 7PB2 | PTA-11184 |

TABLE 2-continued

*Poa bulbosa* Cultivar Accession Numbers.

| Cultivar | ATCC Accession No: |
| --- | --- |
| 7PB42 | PTA-11229 |
| 7PB48 | PTA-11185 |
| 7PB51 | PTA-11230 |
| 7PB55 | PTA-11186 |

Methods of Use

The hybrid cultivars of *Poa bulbosa* described herein can be used in any suitable turf application, e.g., sports field turf, park turf, lawn turf, golf green, golf fairway, sod, gardens, and the like. In some embodiments, the new hybrid cultivars can be used in alternative settings, such as in ditches, hillsides, and roadsides to reduce dust or erosion. The new *Poa bulbosa* hybrid cultivars have utility as cool season grass, and particularly as a cool season component of a turf that also comprises a warm season grass, providing a turf that remains green over a longer period of time than a turf containing only one seasonal grass and/or a traditional warm season grass overseeded with conventional warm season grasses such as ryegrass. The hybrid cultivars are also useful as parental lines to produce hybrid progeny possessing a desired trait of the parent.

Products of Manufacture

Plants and plant portions, including, seed, bulblets, cuttings, tissue cultures, and the like, can be obtained from the described cultivars of *Poa bulbosa* and packaged, for example, in a kit for purposes of commercial reproduction and sale. The plants and plant portions can be packaged to contain an individual *Poa bulbosa* hybrid cultivar type, or a mixture of two or more hybrid *Poa bulbosa* cultivar types. In some embodiments, the packaging or kit can also contain plants or plant portions of at least one non-*Poa bulbosa* variety, for example, that of a warm season grass such as St. Augustine, Zoysia, or Centipede grass. The packaging or kit can be labeled and/or otherwise comprise instructions for planting or overseeding with the enclosed *Poa bulbosa* cultivar tissue.

The hybrid cultivars of *Poa bulbosa* can be used to produce sod, harvested using known methods for use in sod applications, such as lawn production, building materials, and the like

EXAMPLES

The following Examples are provided as representative and are not intended to limit the scope of the invention.

Example 1

Collection of Native *Poa bulbosa*

More than 100 individual native plants, bulbs, and/or bulblets of *Poa bulbosa* were collected and planted in the field for evaluation. These plant lines were initially evaluated in western Oregon for 1) seedling vigor and establishment, 2) vernalization requirements for bulblet production, 3) temperature and photoperiod requirements for bulblet germination, 4) persistence, or re-establishment after comprehensive summer dormancy, 5) acceptable mowing height, 6) fall green-up rates and relative winter activity, 7) disease susceptibilities, and 8) bulblet yield potential, and the like, over a two year post planting period. Plants exhibiting above-average vigor, as well as low relative temperature and photoperiod requirements for bulblet germination and establishment were selected.

Lines were established from the selected plants and used for breeding. Lines with superior performance and elite performing individual plants were selected and hybridized to one another as shown in Table 2. Hybrid cultivars were subsequently selected for improved turf quality, vigor, disease resistance, bulblet yield, and other characteristics, as demonstrated over at least a two-year period. The origin of selected lines used as parental plants for hybridization is shown in Table 3.

One hybrid plant for each of the described crosses in Table 4 was used to establish the *Poa bulbosa* hybrid cultivars. Hybrid plants used to establish each line were selected for desired characteristics, including: proliferated habit; superior winter vigor; low relative temperature and photoperiod requirements sufficient to induce strong, early emergence and establishment of seedlings; definite seasonal flowering; stand persistence and strong re-emergence after warm-season dormancy; and development of a relatively broad crown by producing large numbers of tillers.

TABLE 4

Crosses used to establish hybrid cultivars.

| Maternal Line | Paternal Line(s) | Hybrid Line |
| --- | --- | --- |
| TPb-1 | PI 217500 | 6PB20 |
| TPb-2 | PI 517032 | 6PB22 |
| SIT 237 | CSC200, TPb-6, PI 517032, PI 228404, and 5PB22 (Open pollination) | 6PB25 |
| CSC200 | TPb-2 | 6PB26 |
| TPb-2 | CSC200, TPb-6, PI 517032, PI 228404, 5PB22 (Open pollination) | 6PB27 |
| TPb-6 | CSC200, TPb-2, PI 517032, and PI 228404 | 6PB28 |
| Tpb-3 | CSC200, TPb-2, PI 517032, TPb-6, PI 228404 (Open pollination) | 6PB29 |
| TPb-1 | 6PB25 | 7PB2 |
| CSM 334A | 6PB27 | 7PB42 |
| CSM 333H | PI 254907, PI 217500, CSM 333G, TPb-4 (Open pollination) | 7PB48 |
| CSM 333S | TPb-1 | 7PB51 |
| 6PB20 | PI 254907, PI 217500, CSM 333Z, TPb-4 (Open pollination) | 7PB55 |

TABLE 3

Sources of Parental Lines

| Parental Line | Source |
| --- | --- |
| CSC200 | Single plant from composite bulblet collected near Shasta City, CA; April, 2003 |
| TPb-1 | Single plant collected near Coeur d'Alene, ID; June 2003 |
| TPb-2 | Single plant collected near Coeur d'Alene |
| TPb-3 | Single plant collected near Coeur d'Alene |
| TPb-4 | Single plant collected near Coeur d'Alene |
| TPb-6 | Single plant collected near Coeur d'Alene |
| SIT 237 | Selection from composite bulblet collection near Hood River, OR; March 2004 |
| CSM 333G | Single plant collected from Trinity Mountains, northern CA, March 2006 |
| CSM 333H | Single plant collected from Trinity Mountains |
| CSM 333S | Single plant collected from Trinity Mountains |
| CSM 333Z | Single plant collected from Trinity Mountains |
| CSM 334A | Single plant collected from Trinity Mountains |
| O277 | Single plant from composite bulblet collected as a contaminant in Kentucky bluegrass production fields near Coeur d'Alene |
| 5PB22 | Hybrid Line derived from maternal line PI 302951 and paternal line PI 259763 (U.S. National Germplasm Resources Laboratory). |
| 6PB20 | Hybrid Line derived from maternal line TPb-1 and paternal line PI 217500. |
| 6PB25 | Hybrid Line derived from maternal line SIT 237 open pollinated with CSC200, TPb-6, PI 517032, PI 228404, and 5PB22. |
| PI 217500 | U.S. National Germplasm Resources Laboratory material originating from Pakistan at Saidu, Sivat. |
| PI 228404 | U.S. National Germplasm Resources Laboratory originating from Iran near Ghaverokh. |
| PI 254907 | U.S. National Germplasm Resources Laboratory originating from Iraq near Mosul. |
| PI 517032 | U.S. National Germplasm Resources Laboratory originating from Morocco near Azrou. |
| PI368241 | *Poa pratensis*, U.S. National Germplasm Resources Laboratory originating from Alaska, United States at Agreolymus plot, west field, Palmer. |
| PI230132 | *Poa pratensis*, U.S. National Germplasm Resources Laboratory originating from Iran from south slope of Damavand Mountain, Alborz Range. |
| PI440608 | *Poa pratensis*, U.S. National Germplasm Resources Laboratory originating from Kazakhstan at Victory Collective Farm Orchard near Chimkent. |

Example 2

Cultivar 6PB20

Hybrid 6PB20 seedlings were planted in the field for observation, comparison, and selection in the fall. Verdure was dark green in color, leaves exhibited a fine texture, and plants grew rapidly and mowed cleanly. Plants expressed an erect plant growth habit and performed well during the establishment year under medium to high fertility (fertility is used to mean management of turf grass, including fertilizer, moisture, mowing frequency, herbicide, and the like) in private Bermudagrass over-seeded golf fairway settings at Mississippi State University and Texas Tech. University, and at medium fertility in a private trial at a research location in Western Oregon, demonstrating good stand persistence. This hybrid cultivar was selected for its persistence versus other seedlings and used in continued breeding methods to develop further cultivars with improved texture qualities.

Example 3

Cultivar 6PB22

Hybrid 6PB22 seedlings were planted in the field for observation, comparison, and selection in the fall. Verdure was gray-green in color, leaves were medium textured, and plants grew rapidly and mowed cleanly. Plants expressed a semi-erect plant growth habit. Plants performed well during the establishment year under medium to high fertility in a Bermudagrass over-seeded sports turf setting in Quartzsite, Ariz., in private Bermudagrass over-seeded golf fairway settings at Mississippi State University and Texas Tech. University, and at medium fertility in a private trial at a research location in Western Oregon. This cultivar was selected for its relatively high mid-season activity rate and vigor versus other seedlings, and was used as parent for subsequent hybridization to carry these traits forward into new hybrid cultivars.

Example 4

Cultivar 6PB25

Hybrid 6PB25 seedlings were planted in the field for observation, comparison, and selection in the fall. Verdure was light green in color, leaves were medium textured, and plants grew rapidly and mowed cleanly. Plants expressed a semi-prostrate plant growth habit. Plants performed well under medium to high fertility in private Bermudagrass overseeded golf fairway settings at Mississippi State University and Texas Tech. University, and at medium fertility in a private trial at a research location in Western Oregon. This cultivar was selected for its relatively high activity rate and vigor versus other seedlings and relatively early transition-in from summer dormancy. 6PB25 was used as parent for subsequent hybridization to carry these traits forward into new hybrid cultivars.

Example 5

Cultivar 6PB26

Hybrid 6PB26 seedlings were planted in the field for observation, comparison, and selection in the fall. Verdure was dusky gray-blue-green in color, leaves were medium textured, and plants grew rapidly and mowed cleanly. Plants expressed a semi-erect habit and an erect, oblong-shaped panicle having intermediate compactness. Plants performed well with a high activity rate and good vigor under medium to high fertility in a Bermudagrass over-seeded sports turf setting in private Bermudagrass over-seeded golf fairway settings at Mississippi State University and Texas Technology University, and at medium fertility in a private trial at a research location in Western Oregon.

This cultivar contains a good combination of characteristics, was selected for its good persistence (greater than 50% reemergence) demonstrated in third year spaced plantings and in second year of turf stand, and/or for its nice color, good activity rate, vigor, and spread. It has been used as a parent for subsequent hybridization to carry these traits forward into new hybrid cultivars.

Example 6

Cultivar 6PB27

6PB27 was derived from an open-pollinated hybridization with maternal line TPb-2, involving paternal sources CSC200, TPb-6, PI 517032, PI 228404, and 5PB22. TPb-2 was a single plant selection originally collected from around Coeur d'Alene, Id. in June 2003. The maternal TPb-2 plant, along with the above-mentioned paternal lines, were single plant selections isolated in an indoor, regulated hybridization chamber in May 2005.

Hybrid progeny from the maternal TPb-2 were planted in trays and subsequently planted in the field for observation, comparison and selection in the fall of 2005. The hybrid plant designated 6PB27 was selected on the basis of proliferated habit, superior, winter vigor, low relative temperature and photoperiod requirements sufficient to induce strong, early emergence and establishment of seedlings, definite seasonal flowering, stand persistence and strong re-emergence after warm-season dormancy, and development of a relatively broad crown by producing large numbers of tillers.

Plants expressed a semi-erect habit and a nodding, oblong-shaped panicle having intermediate compactness. Verdure was blue-green in color, and plants grew rapidly, mowed cleanly, and performed well under medium to high fertility in a private Bermudagrass over-seeded golf fairway setting at Mississippi State University and Texas Tech. University, and at medium fertility in a private trial at a research location in Western Oregon.

6PB27 was compared to plants grown from U.S. National Germplasm Resources Laboratory *Poa bulbosa* accession PI 407634 wild type material originating from Turkey. 6PB27 plants and PI 407634 plants were grown at a research location near Corvallis, Oreg. on silty clay loam. The heading date of 6PB27 was about 2 days later than PI 407634. 6PB27 flag leaf height was about 10.6 cm taller and overall plant height was about 11.4 cm taller than PI 407634.

A single plot was planted and evaluated for quality in turf, progeny increase, and PVP trial were planted at Radix Research, Inc.'s farm location near Corvallis, Oreg. in the fall of 2006. Bulblets from the progeny increase nursery of 6PB27 were used for further replicated turf quality testing in a private 2007 Mississippi State University trial at Mississippi State, Mississippi, and a private 2009 Texas Tech. University trial at Lubbock, Tex.

Breeder seed bulblets were first produced in 2006. 2006 Breeder seed bulblets were used to plant a progeny increase. The bulblets from this progeny increase were used to plant a Breeder increase near Potlatch, Id. Seed bulblets from this Breeder increase will be used to plant commercial production fields in the Eastern Washington production areas. 6PB27 is stable and uniform, as propagated from aerial, maternally-clonal bulblets. Each generation of the 6PB27 varietal multiplication phase has resulted in 0% variants and off-types. All breeding and varietal finish work was undertaken at Radix Research's farm location near Corvallis, Oreg., USA and concluded during 2006.

Cultivar 6PB27 contains a good combination of characteristics, and was selected for its good persistence (greater than 50%) demonstrated in third year spaced plantings and in second year of turf stand. It reemerges relatively early and transitions out relatively late, providing a longer active season to match with certain warm season grasses, such as Bermuda grass. 6Pb27 produces a high number of vegetative tillers relative to reproductive tillers during its reproductive phase, resulting in less steaminess in a turf setting. It has been used as a parent for subsequent hybridization to carry these traits forward into new hybrid cultivars.

Example 7

Cultivar 6PB28

Hybrid 6PB28 seedlings were planted in the field for observation, comparison, and selection in the fail. Verdure was vibrant (bright) with a lush green color, leaves were medium textured, and plants grew rapidly and mowed cleanly. Plants performed well under medium to high fertility in private Bermudagrass over-seeded golf fairway settings at Mississippi State University and Texas Tech. University, and at medium fertility in a private trial at a research location in Western Oregon. This cultivar was selected for its desirable lush, vibrant green color and rapid emergence. It has been used as a parent for subsequent hybridization to carry these traits forward into new hybrid cultivars.

Example 8

Cultivar 6PB29

Hybrid cultivar 6Pb29 was seeded in trays and seedlings were subsequently planted in the field for observation, comparison, and selection in the fall. Verdure was blue-green in color, leaves were medium textured, and plants grew rapidly and mowed cleanly. Plants expressed a semi-erect habit and a nodding, oblong-shaped panicle having intermediate compactness, and exhibits early transition into dormancy. Plants performed well under medium to high fertility in private Bermudagrass over-seeded golf fairway settings at Mississippi State University and Texas Technology University, and at medium fertility in a private trial at a research location in Western Oregon.

The cultivar demonstrated persistence (approximately 50%) in two years of both turf stand and spaced plot plantings. The cultivar exhibits very high activity rate and vigor. It also demonstrates a high number of vegetative tillers during its reproductive period, resulting in low steaminess in a turf stand. It has been used as a parent for subsequent hybridization to carry these traits forward into new hybrid cultivars.

Example 9

Cultivar 7PB2

7PB2 was derived from a hybridization between maternal line TPb-1 and paternal hybrid line 6PB25. TPb-1 was a single plant selection originally collected around Coeur d'Alene, Id. in June 2003. 6PB25 was a single plant selection from a 2005 hybridization that traces back to maternal line SIT 237, a selection from a composite of seed originally collected from plants in and around Hood River, Oreg. in March 2004.

The maternal TPb-1 plant, along with paternal line 6PB25 were single plant selections isolated in an indoor, regulated hybridization chamber in May 2006. Hybrid progeny from the maternal TPb-1 were planted in trays and subsequently planted in the field for observation, comparison and selection in the fall of 2006. One hybrid plant, 7PB2, was selected on the basis of proliferated panicle habit, superior winter vigor, low relative temperature and photoperiod requirements sufficient to induce strong, early emergence and establishment of seedlings, definite seasonal flowering, stand persistence and strong re-emergence after warm-season dormancy. Verdure was vibrant (bright) and dark-green in color, the color having a familiar ryegrass look. Leaves were medium textured, and plants grew rapidly and mowed cleanly. Plants expressed a semi-prostrate habit and a nodding, ovate-shaped, open panicle, and performed well under medium fertility in a private trial at Radix Research's location in Western Oregon.

Plots were planted and evaluated for quality in turf and a progeny increase and PVP trial were planted at Radix Research, Inc.'s farm location near Corvallis, Oreg. in the fall of 2008. Seed bulblets from the progeny increase nursery of 7PB2 was used for further replicated turf quality testing.

Breeder seed bulblets were first produced in 2007. 2008 Breeder seed bulblets were used to plant a progeny increase. The bulblets from this progeny increase were used to plant a Breeder seed increase near Potlatch, Id. Seed bulblets from this Breeder increase will be used to plant commercial seed production fields in the Eastern Washington production areas. 7PB2 is stable and uniform due to the 'seed' used being from aerial, maternally-clonal bulblets. Each generation of the 7PB2 varietal multiplication phase has resulted in 0% variants and off-types.

This cultivar demonstrated very good and reliable bulblet yield and germination. The bulblets have an oval shape needing minimal processing and cleanup. The plants have a good activity rate and persistence, with a rapid, relatively early transition both into and out of dormancy. Persistence (greater than 60%) has been demonstrated for two years in a turf setting and for three years in spaced plantings. It has been used as a parent for subsequent hybridization to carry these traits forward into new hybrid cultivars.

Example 10

Cultivar 7PB42

Hybrid cultivar 7Pb42 was seeded in trays and subsequently planted in the field for observation, comparison, and selection in the fall. Verdure was a combination of blue-green-gray color, leaves were medium textured, and plants grew rapidly and mowed cleanly. Plants expressed a semi-erect habit and a nodding, oblong-shaped panicle having intermediate compactness. Plants performed well under medium to high fertility in a private, Bermudagrass over-seeded, golf fairway setting at Texas Tech. University and at medium fertility in a private trial at a research location in Western Oregon.

This cultivar contains a good combination of desirable characteristics, and was selected for its good persistence (greater than 50%) demonstrated in third year spaced plantings and in second year of turf stand. This cultivar exhibits an early transition-in to active season. 6Pb42 produces a high number of vegetative tillers relative to reproductive tillers during its reproductive phase, resulting in less steaminess in a turf setting. It has been used as a parent for subsequent hybridization to carry these traits forward into new hybrid cultivars.

Example 11

Cultivar 7PB48

Hybrid cultivar 7Pb48 was seeded in trays and subsequently planted in the field for observation, comparison, and selection in the fall. 7PB48 plants exhibited a vibrant (bright) and dark green verdure, grew rapidly, and mowed cleanly. Plants expressed a semi-erect plant growth habit and an erect, narrow, tapering panicle having intermediate compactness. 7PB48 plants performed well under medium to high fertility in a private, Bermudagrass over-seeded, golf fairway setting at Texas Technology University, and at medium fertility in a private trial at a research location in Western Oregon, demonstrating good persistence in a turf setting.

This cultivar demonstrated very good persistence (at least 80%) over three years in spaced plantings and in two years in turf stand. 7PB48 transitions into its active winter season relatively early and transitions out of active growth into dormancy relatively late. Such a transition time pattern results in a longer active season that complements a companion grass such as Bermudagrass. This hybrid cultivar has several additional commercially desirable characteristics including bright dark green color, medium-to fine leaf texture, and good density. It has been used as a parent for subsequent hybridization to carry these traits forward into new hybrid cultivars.

Example 12

Cultivar 7PB51

Hybrid cultivar 7Pb51 was seeded in trays and subsequently planted in the field for observation, comparison, and selection in the fall. Verdure was blue-green in color, leaves were medium textured, and plants grew rapidly and mowed cleanly. Plants expressed a semi-prostrate plant growth habit and a nodding, oblong-shaped panicle having intermediate compactness. Plants performed well under medium fertility in a private Bermudagrass over-seeded turf setting at a research location in Western Oregon.

This cultivar demonstrated very good persistence (at least 70%) over three years in spaced plantings and in two years in turf stand. 7PB51 exhibits a high activity rate and an early transition-in to active season. The cultivar produces a high number of vegetative tillers relative to reproductive tillers during its reproductive phase, resulting in less steaminess in a turf setting. It has several additional commercially desirable characteristics including medium leaf texture, and good density. It has been used as a parent for subsequent hybridization to carry these traits forward into new hybrid cultivars.

Example 13

Cultivar 7PB55

7PB55 was derived from an open-pollinated hybridization with maternal line 6PB20, involving paternal sources PI 254907, PI 217500, CSM 333Z, and TPb-4. Maternal line 6PB20 was a single plant selection from a 2005 hybridization that traces back to maternal line TPb-1, a selection originally collected around Coeur d'Alene, Id. in June 2003. These lines and many others were evaluated in western Oregon for 1) seedling vigor and establishment, 2) vernalization requirements for seed bulblet production, 3) temperature and photoperiod requirements for seed bulblet germination, 4) persistence, or reestablishment after comprehensive summer dormancy, 5) acceptable mowing height, 6) fall green-up rates and relative winter activity, 7) disease susceptibilities, and 8) seed bulblet yield potential.

Hybrid progeny from the maternal 6PB20 were planted in trays and subsequently planted in the field for observation, comparison and selection in the fall of 2006. One hybrid plant, 7PB55, was selected on the basis of proliferated habit, superior winter vigor, low relative temperature and photoperiod requirements sufficient to induce strong, early emergence and establishment of seedlings, definite seasonal flowering, stand persistence and strong re-emergence after warm-season dormancy, and development of a relatively broad crown by producing large numbers of tillers, and a dark green verdure. 7PB55 plants grew rapidly, mowed cleanly, and performed well at medium fertility in a private trial at Radix Research's location in Western Oregon.

Hybrid cultivar 7Pb55 was seeded in trays and subsequently planted in the field for observation, comparison, and selection in the fall. 7PB55 plants exhibited a vibrant (bright) and dark green verdure, narrow width of leaves, grew rapidly, and mowed cleanly. Plants expressed an erect plant growth habit and an erect, narrow, tapering panicle having intermediate compactness. 7PB55 plants performed well under medium to high fertility in a private, Bermudagrass over-seeded, golf fairway setting at Texas Tech. University, and at medium fertility in a private trial at a research location in Western Oregon, demonstrating good persistence in a turf setting.

Plots were planted and evaluated for quality in turf and a progeny increase and PVP trial were planted at Radix Research, Inc.'s farm location near Corvallis, Oreg. in the fall of 2008. Seed bulblets from the progeny increase nursery of 7PB55 was used for further replicated turf quality testing.

Evidence of Uniformity and Stability: Breeder seed bulblets were first produced in 2007. 2008 Breeder seed bulblets were used to plant a progeny increase. The bulblets from this progeny increase were used to plant a Breeder seed increase near Potlatch, Id. Seed bulblets from this Breeder increase will be used to plant commercial seed production fields in the Eastern Washington production areas. 7PB55 is stable and uniform due to the 'seed' used being from aerial, maternally-clonal bulblets. Each generation of the '7PB55' varietal multiplication phase has resulted in 0% variants and off-types.

This cultivar demonstrated very good persistence (at least 80%) over three years in spaced plantings and in two years in turf stand. 7PB55 transitions into its active season relatively early and transitions out of active growth into dormancy relatively late, resulting in a longer active season to match with a companion grass such Bermudagrass. It has several additional commercially desirable characteristics including bright dark green color, medium-to fine leaf texture, good density. It has been used as a parent for subsequent hybridization to carry these traits forward into new hybrid cultivars.

Example 14

Turf Grass Trait Evaluation

In Examples 16 and 17 below, wild type collections of *Poa bulbosa* PI 407634, O277, and SIT 237, as well as the cool-season perennial ryegrass varieties 'LineDrive GLS' from ProSeeds Marketing (Jefferson, Oreg.) and 'Vail II' from Radix Research, Inc., (Corvallis, Oreg.) were used as controls. In general, a turfgrass rating score of 5 or greater or 50% or greater represents a preferred characteristic is present.

Turf quality ratings and individual turf grass traits for *Poa bulbosa* cultivars 6PB26, 6PB27, and 6PB29 were assessed at a Mississippi State University trial at several time points during the 2007-2008 first year growing season. Turf quality ratings were evaluated based on traditional Turf Ratings, discussed in the Detailed Description above, and shown in the data tables provided. Table 5 shows the average turf quality ratings for cultivars 6PB26, 6PB27, and 6PB29, control *Poa bulbosa* lines PI407634, O277, and SIT 237, as well as the ryegrass line, LineDrive.

Individual turf grass traits were assessed for cultivars 6PB20, 6PB22, 6PB29, 7PB2, 7PB42, 7PB48, 7PB51, and 7PB55 (seeded on Sep. 30, 2008) during the 2008-2009 growing season. The evaluated traits included both "transition-out" of active growth to dormancy at the end of the 2008-2009 growing season (expressed as a percentage) and "transition-in" to active growth from dormancy at the beginning of the 2009-2010 growing season. Steminess, color, overall turf quality, and overall score (equally weighted combination of turf quality, steminess, and color) were also rated. Table 6 shows the turf grass trait ratings for cultivars 6PB29, 7PB2, 7PB42, 7PB48, 7PB51, and 7PB55, control *Poa bulbosa* wild-type lines PI407634, O277, and SIT 237, as well as the ryegrass lines LineDrive and Vail II.

Turf grass traits were also assessed for cultivars 6PB20, 6PB22, 6PB28, 6PB29, 7PB2, 7PB42, 7PB48, 7PB51, and 7PB55 (seeded Sep. 30, 2008) during the 2009-2010 growing season. The evaluated traits included scores for ground cover during November, 2009, steminess score during spring, 2010, average turf quality score over several time points during the 2009-2010 growing season (dates shown in Table 9), color over several time points, and overall turf quality (ground cover, steminess, color, and turf quality). Table 7 shows turf grass ratings for 6PB20, 6PB22, 6PB28, 6PB29, 7PB2, 7PB42, 7PB48, 7PB51, and 7PB55, control *Poa bulbosa* lines PI407634, O277, and SIT 237, as well as ryegrass lines LineDrive (ProSeeds Marketing, Jefferson, Oreg.) and Vail II (Radix Research Inc., Corvallis, Oreg.). Table 8 shows October, 2009, transition in scores and Nov. 30, 2009, ground cover rating for cultivars 6PB20, 6PB22, 6PB28, 6PB29, 7PB2, 7PB42, 7PB48, 7PB51, and 7PB55, control *Poa bulbosa* lines PI407634, O277, and SIT 237, as well as ryegrass lines LineDrive and Vail II over two time points in October, 2009. Table 9 shows average monthly turf grass ratings during November 2009 to March 2010 for 6PB20, 6PB22, 6PB28, 6PB29, 7PB2, 7PB42, 7PB48, 7PB51, and 7PB55, control *Poa bulbosa* lines PI407634, O277, and SIT 237, as well as ryegrass lines LineDrive and Vail II planted Sep. 30, 2008.

Post-dormancy re-emergence was evaluated for 6PB20, 6PB22, 6PB26, 6PB27, and 6PB29. Re-emergence was evaluated on Oct. 20, 2007 following the initial planting, the 2006-2007 growing season, and the 2007 warm season dormancy. Table 10 shows the post-dormancy re-emergence scores for 6PB20, 6PB22, 6PB26, 6PB27, and 6PB29, control *Poa bulbosa* lines PI407634, O277, and SIT 237.

Second year post dormancy re-emergence of spaced-plant plots for 6PB26, 6PB27, 6PB29, and 7PB2 (seeded Nov. 17, 2007) was evaluated. Re-emergence was evaluated as percent green over three time points after the 2008 warm season dormancy. Table 11 shows the percent re-emergence for 6PB26, 6PB27, 6PB29, 7PB2, and control *Poa bulbosa* line O277.

Green plot cover was assessed during the transition out period for 6PB20, 6PB22, 6PB26, 6PB27, and 6PB29 when used to overseed Bermudagrass. Percent green plot cover was assessed over three time points at the end of the 2007-2008 growing season. Table 12 shows the percent green plot cover for 6PB20, 6PB22, 6PB26, 6PB27, and 6PB29, control *Poa bulbosa* lines PI407634, O277, and SIT 237, as well as ground cover during establishment of ryegrass line LineDrive. Table 12 shows that *Poa bulbosa* lines transition out while Bermudagrass transitions in, causing the turf plot to retain some green ground cover during the transition. By June 25, the Bermudagrass has fully transitioned in from dormancy.

Percent germination was assessed over three time points following planting on Aug. 28, 2009. Table 13 shows the percent germination for 6PB20, 6PB22, 6PB29, 7PB2, 7PB42, 7PB48, 7PB51, and 7PB55, and control *Poa bulbosa* lines PI407634, O277, and SIT 237.

Color was assessed for 6PB20, 6PB22, 6PB26, 6PB27, and 6PB29 over the 2007-2008 growing season in a Mississippi State University turf trial. Table 14 shows the color rating for 6PB20, 6PB22, 6PB26, 6PB27, and 6PB29, control *Poa bulbosa* lines PI407634, O277, and SIT 237, as well as ryegrass line LineDrive, over four time points.

TABLE 5

2007-2008 Turf Quality Ratings.

| Line | Nov. 16, 2007 | Nov. 28, 2007 | Dec. 10, 2007 | Dec. 19, 2007 | Jan. 7, 2008 | Jan. 28, 2008 | Feb. 8, 2008 | Feb. 28, 2008 |
|---|---|---|---|---|---|---|---|---|
| PI 407634 | 5 | 6 | 6.3 | 7 | 6.7 | 6.3 | 6.3 | 7.3 |
| O277 | 5 | 6 | 7 | 7 | 7 | 6.3 | 7 | 6.7 |
| SIT 237 | 4.3 | 5 | 6 | 6.7 | 6.7 | 6.3 | 7 | 6.3 |
| 6PB20 | 4 | 3.3 | 4.7 | 6 | 5.7 | 5.3 | 6 | 6 |
| 6PB22 | 5 | 6 | 6 | 7 | 7 | 7 | 7.3 | 7 |
| 6PB26 | 5 | 5.7 | 6 | 7 | 6.7 | 7 | 7 | 7.3 |
| 6PB27 | 5.7 | 6 | 7 | 7 | 7.7 | 7.7 | 8 | 8 |
| 6PB29 | 5 | 6 | 6 | 6.7 | 7 | 6.7 | 7.7 | 7.3 |
| LineDr | 6 | 6.3 | 6.7 | 7 | 7 | 7 | 7.7 | 8 |

| Line | Mar. 12, 2008 | Mar. 31, 2008 | Apr. 10, 2008 | Apr. 24, 2008 | May 9, 2008 | May 22, 2008 | Jun. 25, 2008 | Mean |
|---|---|---|---|---|---|---|---|---|
| PI 407634 | 7.7 | 6.3 | 6.3 | 5.7 | 3.7 | 4.3 | 6 | 6.1 |
| O277 | 7.3 | 6.3 | 6 | 4.3 | 4 | 4.7 | 6 | 6 |
| SIT 237 | 6.7 | 6 | 4.3 | 4 | 4.7 | 5.7 | 6 | 5.7 |
| 6PB20 | 6 | 6 | 5.3 | 4.3 | 4.3 | 5.3 | 6 | 5.2 |
| 6PB22 | 7 | 6.7 | 6.3 | 5 | 4.3 | 5 | 6 | 6.2 |

TABLE 5-continued 2007-2008 Turf Quality Ratings.

| | | | | | | | | |
|---|---|---|---|---|---|---|---|---|
| 6PB26 | 7 | 6 | 6 | 5 | 4 | 4.7 | 6 | 6 |
| 6PB27 | 7.7 | 7 | 5.7 | 3.7 | 4 | 5 | 6 | 6.4 |
| 6PB29 | 7.3 | 6.7 | 5 | 4.3 | 4.3 | 5.3 | 6 | 6.1 |
| LineDr | 8 | 7.7 | 7.7 | 8 | 8 | 7 | 3.7 | 7 |

TABLE 6

2008-2009 turf trait ratings for plots seeded Sep. 30, 2008.

| Line | 2009 Transition in score | 2008 Transition out (%) | Steminess score | Color score | Turf quality score | Overall score |
|---|---|---|---|---|---|---|
| PI 407634 | 2.5556 | 38.333 | 5.1111 | 4.5 | 5 | 4.8704 |
| O277 | 3.7778 | 38.333 | 4.8889 | 6 | 4.7143 | 5.2011 |
| SIT 237 | 5.2222 | 50 | 3.6667 | 6 | 5.8571 | 5.1746 |
| 6PB20 | 4.8889 | 36.778 | 7 | 4.6667 | 6.0476 | 5.9048 |
| 6PB22 | 3.2222 | 38.333 | 5.4444 | 5.3333 | 5.7143 | 5.4974 |
| 6PB28 | 4.3333 | 60.000 | 3.7778 | 6.0000 | 6.0952 | 5.2910 |
| 6PB29 | 4.8889 | 58 | 8.2222 | 4.1667 | 5.7143 | 6.0344 |
| 7PB2 | 6 | 66.556 | 4.4444 | 7 | 6.5714 | 6.0053 |
| 7PB42 | 5.2222 | 43.667 | 7 | 5.5 | 5.5714 | 6.0238 |
| 7PB48 | 7.3333 | 33 | 5.4444 | 6.5 | 5.7143 | 5.8862 |
| 7PB51 | 5.3333 | 50.111 | 6.3333 | 5.1667 | 5.5238 | 5.6746 |
| 7PB55 | 7.3333 | 36.111 | 5.2222 | 6.5 | 6 | 5.9074 |
| LineDrive | 4.7778 | 1 | 9 | 7.8333 | 7.8095 | 8.2143 |
| Vail II | 4.3333 | 1 | 9 | 8 | 7.0952 | 8.0317 |

TABLE 7

2009-2010 Turf Trait Ratings for plots seeded Sep. 30, 2008.

| Line | Steminess score | Texture score Jan. 20, 2010 | Color Score Nov. 16, 2009 | Color Score Feb. 2, 2010 | Color Score Mar. 24, 2010 | Average Turf quality score | Overall score |
|---|---|---|---|---|---|---|---|
| PI 407634 | 4.5 | 6 | 5 | 4.6667 | 5.3333 | 1.4242 | 2.2889 |
| O277 | 6 | 6 | 5 | 5 | 5.6667 | 3.697 | 4.1778 |
| SIT 237 | 4.6667 | 7 | 5 | 5.6667 | 5.3333 | 4.9697 | 4.9778 |
| 6PB20 | 6.3333 | 9 | 5.3333 | 4 | 3.3333 | 3.9697 | 4.3778 |
| 6PB22 | 6 | 5.3333 | 4.6667 | 4 | 5 | 4.2727 | 4.5111 |
| 6PB28 | 5 | 6 | 5 | 5 | 4.6667 | 2.8182 | 3.4 |
| 6PB29 | 7.6667 | 5.3333 | 5 | 3.3333 | 4.3333 | 4.1515 | 4.6222 |
| 7PB2 | 5 | 6.3333 | 6 | 6.6667 | 3.6667 | 5.4242 | 5.4889 |
| 7PB42 | 5.3333 | 5 | 6 | 4 | 5 | 5 | 5.0444 |
| 7PB48 | 7.3333 | 7.6667 | 6.3333 | 6.6667 | 6.3333 | 6.2727 | 6.4444 |
| 7PB51 | 7.1667 | 5.6667 | 6 | 4 | 5.3333 | 5.0303 | 5.3111 |
| 7PB55 | 7.6667 | 8 | 7 | 7 | 6.3333 | 6.2121 | 6.5111 |
| LineDrive | 9 | 7 | 4 | 6.6667 | 8 | 5.6364 | 6.0444 |
| Vail II | 9 | 7 | 4 | 7 | 8 | 5.0909 | 5.6667 |

TABLE 8

2009-2010 Transition In/and Ground Cover - plots seeded Sep. 30, 2008.

| Line | Transition In Oct. 10, 2009 | Transition In Oct. 26, 2009 | Ground Cover Nov. 30, 2009 |
|---|---|---|---|
| PI 407634 | 2 | 3.3333 | 2.3333 |
| O277 | 2 | 4.3333 | 5 |
| SIT 237 | 4.3333 | 6 | 5.3333 |
| 6PB20 | 4.3333 | 5.3333 | 5 |
| 6PB22 | 1 | 4 | 4.6667 |
| 6PB28 | 5.3333 | 5.3333 | 2.3333 |
| 6PB29 | 3.6667 | 5.3333 | 5.6667 |
| 7PB2 | 4.6667 | 7 | 6.3333 |
| 7PB42 | 3.3333 | 6 | 6.3333 |
| 7PB48 | 6.3333 | 8 | 7.6667 |
| 7PB51 | 3 | 6.3333 | 6.6667 |
| 7PB55 | 6.6667 | 8 | 7.3333 |
| LineDrive | 3.3333 | 4 | 7 |
| Vail II | 3 | 4 | 6 |

TABLE 9

2009-2010 Turf Quality Ratings for plots seeded Sep. 30, 2008.

| Line | November 2009 Average | December 2009 Average | January 2010 Average | February 2010 Average | March 2010 Average |
|---|---|---|---|---|---|
| PI 407634 | 1.665 | 1 | 1 | 1.33 | 1.665 |
| O277 | 3 | 4.165 | 3.835 | 3.665 | 3.165 |
| SIT 237 | 4.33 | 4.835 | 5.165 | 5.5 | 4.83 |
| 6PB20 | 3.17 | 4.33 | 4 | 4.33 | 3.5 |
| 6PB22 | 3.335 | 4.33 | 4.5 | 4.665 | 4.33 |
| 6PB28 | 3 | 2.165 | 2.165 | 3.5 | 3.5 |
| 6PB29 | 3.665 | 4.33 | 4.335 | 3.67 | 4 |
| 7PB2 | 4.835 | 5.165 | 6.165 | 5.835 | 4.665 |
| 7PB42 | 4 | 5 | 5.5 | 5 | 4.835 |
| 7PB48 | 5.335 | 5.67 | 6.67 | 6.5 | 6.5 |
| 7PB51 | 4.17 | 4.835 | 5.5 | 4.835 | 5 |
| 7PB55 | 5.335 | 5.67 | 6 | 6.83 | 6.665 |

TABLE 9-continued 2009-2010 Turf Quality Ratings for plots seeded Sep. 30, 2008.

| Line | November 2009 Average | December 2009 Average | January 2010 Average | February 2010 Average | March 2010 Average |
|---|---|---|---|---|---|
| LineDrive | 4.165 | 5 | 5.165 | 6.17 | 7 |
| Vail II | 3.835 | 4 | 5 | 5.5 | 6.67 |

TABLE 10

2007 - 2nd year re-emergence and plant vigor/activity scores.

| Line | Re-emergence score | Plant vigor/activity rate |
|---|---|---|
| PI 407634 | 6 | 3 |
| O277 | 4 | 3 |
| SIT 237 | 5 | 6 |
| 6PB20 | 6 | — |
| 6PB22 | 8 | — |
| 6PB26 | 7 | 7 |
| 6PB27 | 7 | 6 |
| 6PB29 | 8 | 8 |

TABLE 11

2008 % re-emergence over time for plots seeded Nov. 17, 2007

| Line | Sep. 3, 2008 | Oct. 8, 2008 | Nov. 4, 2008 |
|---|---|---|---|
| O277 | 0 | 2 | 10 |
| 6PB26 | 0 | 2 | 43 |
| 6PB27 | 4 | 13 | 59 |
| 6PB29 | 15 | 25 | 70 |
| 7PB2 | 0 | 4 | 48 |

TABLE 12

2008 % green plot cover in over-seeded turf

| Line | Apr. 24, 2008 | May 9, 2008 | Jun. 25, 2008 |
|---|---|---|---|
| PI 407634 | 85 | 50 | 98 |
| O277 | 53.3 | 61.7 | 97 |
| SIT 237 | 53.3 | 73.3 | 98 |
| 6PB20 | 58.3 | 58.3 | 97 |
| 6PB22 | 76.7 | 55 | 98 |
| 6PB26 | 70 | 53.3 | 98 |
| 6PB27 | 33.3 | 56.7 | 96 |
| 6PB29 | 48.3 | 61.7 | 98 |
| LineDrive | 99 | 99 | 99 |

TABLE 13

Percent germination for plots seeded Aug. 28, 2009.

| Line | Sep. 16, 2009 | Oct. 20, 2009 | Oct. 28, 2009 |
|---|---|---|---|
| PI 407634 | 0 | 69 | 86 |
| O277 | 0 | 10 | 47 |
| SIT 237 | 0 | 11 | 64 |
| 6PB26 | 0 | 33 | 67 |
| 6PB27 | 0 | 72 | 78 |
| 6PB29 | 0 | 58 | 76 |
| 7PB2 | 0 | 25 | 51 |
| 7PB42 | 0 | 89 | 92 |
| 7PB48 | 0 | 19 | 70 |
| 7PB51 | 0 | 89 | 92 |
| 7PB55 | 0 | 14 | 64 |

TABLE 14

2007-2008 growing season color rating.

| Line | Jan. 11, 2008 | Feb. 28, 2008 | Mar. 20, 2008 | Apr. 10, 2008 | Mean rating |
|---|---|---|---|---|---|
| PI 407634 | 6 | 6 | 5.7 | 6 | 5.9 |
| O277 | 6 | 6 | 6 | 5 | 5.8 |
| SIT 237 | 6.7 | 5 | 5.3 | 3.7 | 5.2 |
| 6PB20 | 5 | 5.3 | 5.7 | 5 | 5.3 |
| 6PB22 | 6 | 6 | 6.7 | 6.3 | 6.3 |
| 6PB26 | 6 | 6 | 6.7 | 5.7 | 6.1 |
| 6PB27 | 6 | 6 | 6 | 4.7 | 5.7 |
| 6PB29 | 6 | 6 | 6 | 5 | 5.8 |
| LineDrive | 8 | 8 | 8 | 8 | 8 |

Example 17

Cultivar Trait Measurements

Cultivar plant characteristics were measured during the growing seasons of 2006-2007, 2007-2008, and 2008-2009. Tables 15-17 show measurements taken for each of the indicated growing seasons. Plant height, flag leaf height, flag leaf length, subtending leaf length, particle length, and crown diameter are expressed in centimeters. Flag leaf width, subtending leaf width, vegetative leaf width, live bulblet length, and dry bulb width are expressed in millimeters. Dry bulb weight and dry bulblet/seed weight are expressed in grams per 10,000.

TABLE 15

2007 plant characteristics.

| Line | Plant height | Flag leaf height | Flag leaf length | Flag leaf width | Subtending leaf length | Subtending leaf width | Panicle length | Vegetative leaf width | Bulblet length |
|---|---|---|---|---|---|---|---|---|---|
| PI 407634 | 41 | 23.9 | 5.1 | 4 | 6.8 | 4.7 | 9.4 | 3.2 | 15.8 |
| O277 | 47.2 | 30.1 | 6.1 | 4 | 8.3 | 4.8 | 9.7 | 3.1 | 13.2 |
| SIT 237 | 45.9 | 25.9 | 3.2 | 3.6 | 5.4 | 4.2 | 10.5 | 2.9 | 21.1 |
| 6PB26 | 50.2 | 26.8 | 6.1 | 4.1 | 7.6 | 4.7 | 9.4 | 3.6 | 23.2 |
| 6PB27 | 56.7 | 34.5 | 9.3 | 5.5 | 11.5 | 5.9 | 15.4 | 3.4 | 19.1 |
| 6PB29 | 56.7 | 36.7 | 6.8 | 4.2 | 9.9 | 5.4 | 15.2 | 3.8 | 17.3 |

TABLE 16

2008 plant characteristics.

| Line | Plant height | Flag leaf height | Flag leaf length | Flag leaf width | Subtending leaf length | Subtending leaf width | Panicle length | Bulblet length | Dry bulb weight | Dry bulb width |
|---|---|---|---|---|---|---|---|---|---|---|
| PI 447634 | 47.5 | 25.5 | 3.1 | 3.6 | 4.5 | 4.3 | 6.3 | 24.6 | 41.5 | 1.99 |
| O277 | 45.9 | 29.1 | 5.3 | 4.2 | 7.8 | 4.9 | 8.7 | 25 | 44.5 | 2.01 |
| SIT 237 | 55.7 | 34.7 | 3.3 | 3.1 | 5.4 | 4 | 8.8 | 22.3 | 40.5 | 1.84 |
| 6PB26 | 59.7 | 36.3 | 5.1 | 3.5 | 7.2 | 4.6 | 7.9 | 20.1 | 41.5 | 1.97 |
| 6PB27 | 53.1 | 37.7 | 6.3 | 4.7 | 8.4 | 5.3 | 11.6 | 18.6 | 42 | 2.01 |
| 6PB29 | 59.2 | 39.6 | 7.4 | 4.8 | 9.1 | 5.4 | 14.7 | 25 | 40.5 | 1.91 |

TABLE 17

2009 plant characteristics for plots seeded Sep. 30, 2008.

| Line | Plant height | Flag leaf height | Flag leaf length | Flag leaf width | Subtending leaf length | Subtending leaf width |
|---|---|---|---|---|---|---|
| PI 407634 | 41.4 | 24.3 | 4.8 | 4.1 | 6.6 | 4.6 |
| O277 | 46.6 | 29.5 | 5.9 | 4 | 8.6 | 4.9 |
| SIT 237 | 46.5 | 26.2 | 3.2 | 3.5 | 5.5 | 4.1 |
| 7PB2 | 33.4 | 19.3 | 3 | 4.2 | 4.7 | 4.5 |
| 7PB42 | 55.3 | 33.1 | 9.8 | 5.4 | 11 | 5.7 |
| 7PB48 | 40.8 | 20.9 | 3.8 | 2.1 | 6.4 | 2.1 |
| 7PB51 | 38.8 | 20.3 | 7.7 | 4.7 | 9.2 | 5.3 |
| 7PB55 | 41.8 | 21.3 | 4 | 2.2 | 6.6 | 2.4 |

| Line | Panicle length | Vegetative leaf width | Bulblet length | Dry bulb weight | Dry bulb width | Dry seed weight |
|---|---|---|---|---|---|---|
| PI 407634 | 9.6 | 3.1 | 15 | 34.8 | 1.98 | NA |
| O277 | 10 | 2.9 | 13.8 | 37.1 | 2.04 | NA |
| SIT 237 | 10.7 | 3 | 20.7 | 32.1 | 1.78 | NA |
| 7PB2 | 8.9 | 3.1 | 15.1 | 28.3 | 1.67 | NA |
| 7PB42 | 15 | 3.5 | 20.2 | 31.2 | 2.03 | NA |
| 7PB48 | 8.1 | 1.5 | 12.5 | 27.4 | 1.5 | NA |
| 7PB51 | 11.5 | 3.4 | 19.3 | 29.6 | 1.94 | NA |
| 7PB55 | 8.3 | 1.4 | 15.9 | 25.6 | 1.59 | NA |

What is claimed is:

1. A hybrid *Poa bulbosa* cultivar selected from the group consisting of:
   6PB20 (A.T.C.C. Accession No. PTA-11181);
   6PB22 (A.T.C.C. Accession No. PTA-11228);
   6PB25 (A.T.C.C. Accession No. PTA-11182);
   6PB26 (A.T.C.C. Accession No. PTA-11183);
   6PB27 (A.T.C.C. Accession No. PTA-11187);
   6PB28 (A.T.C.C. Accession No. PTA-11188);
   6PB29 (A.T.C.C. Accession No. PTA-11189);
   7PB2 (A.T.C.C. Accession No. PTA-11184);
   7PB42 (A.T.C.C. Accession No. PTA-11229);
   7PB48 (A.T.C.C. Accession No. PTA-11185);
   7PB51 (A.T.C.C. Accession No. PTA-11230); and
   7PB55 (A.T.C.C. Accession No. PTA-11186).

2. The hybrid *Poa bulbosa* cultivar of claim 1, wherein said hybrid cultivar is a cool season component of a turf that comprises a warm season grass.

3. The hybrid *Poa bulbosa* cultivar of claim 2, wherein the warm season grass is Bermuda grass.

4. Reproductive tissue, bulbs, seed, or bulblets obtained from the hybrid cultivar of claim 1.

5. Turf comprising one or more hybrid cultivar of claim 1.

6. The turf of claim 5, comprising a sports turf, golf fairway, golf green, park, or lawn.

7. An ovule of A bulb of the plant of claim 1.

8. A hybrid *Poa bulbosa* cultivar consisting of 6PB27 (A.T.C.C. Accession No. PTA-11187).

9. A tissue culture consisting of cells or tissue obtained from a leaf, anther, stem, petiole, root, root tip, seed, bulblet, bulb, flower, embryo, or meristematic cell of the hybrid *Poa bulbosa* cultivar of claim 1.

10. A protoplast produced from the plant of claim 9.

11. A *Poa bulbosa* plant regenerated from the tissue culture of claim 9.

12. A kit comprising hybrid *Poa bulbosa* seed or bulblets produced by a hybrid *Poa bulbosa* of claim 1 and seed of a warm season plant.

13. A method for producing an improved *Poa bulbosa* hybrid plant, the method comprising:
   a) selecting a pair of parental plants from the hybrid *Poa bulbosa* cultivars of claim 1; and
   b) inducing hybridization of the parental plants by providing pollen from one of said parental plants to the ovule of the other of said parental plants; and
   c) growing seed produced by the induced hybridization to produce an improved *Poa bulbosa* hybrid plant containing one or more desired characteristic carried forward from one of said parental plants.

14. The method of claim 13, wherein said one or more desired characteristic is selected from the group consisting of:
   a) vibrant verdure;
   b) length of active growth period;
   c) density;
   d) leaf texture; and
   f) comprehensive dormancy.

15. Turf produced from reproductive tissue, bulbs, seeds, or bulblets obtained from one or more hybrid cultivar of claim 1.

16. A hybrid *Poa bulbosa* cultivar consisting of 7PB2 (A.T.C.C. Accession No. PTA-11184).

17. A hybrid *Poa bulbosa* cultivar consisting of 7PB55 (A.T.C.C. Accession No. PTA-11186).

* * * * *